United States Patent
Meessen et al.

(12)

(10) Patent No.: US 6,858,755 B2
(45) Date of Patent: Feb. 22, 2005

(54) PROCESS FOR THE PREPARATION OF UREA

(75) Inventors: Jozef Hubert Meessen, Gulpen (NL); Kees Jonckers, Susteren (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/432,876

(22) PCT Filed: Nov. 23, 2001

(86) PCT No.: PCT/NL01/00854

§ 371 (c)(1),
(2), (4) Date: Oct. 21, 2003

(87) PCT Pub. No.: WO02/46145

PCT Pub. Date: Jun. 13, 2002

(65) Prior Publication Data

US 2004/0054229 A1 Mar. 18, 2004

(30) Foreign Application Priority Data

Dec. 5, 2000 (NL) .............................................. 1016797

(51) Int. Cl.$^7$ ........................................... C07C 273/00
(52) U.S. Cl. ......................................... 564/73; 564/67
(58) Field of Search ...................................... 564/67, 73

(56) References Cited

U.S. PATENT DOCUMENTS 6,084,129 A      7/2000   Romiti

FOREIGN PATENT DOCUMENTS

EP      891 968      1/1999

OTHER PUBLICATIONS

Mavrovic et al., compressing and recovering the exhaust gases from the synthesis of urea, Chemical Abstract, DN 68:95356, (DE 1257769)1968.*

* cited by examiner

*Primary Examiner*—J. Parsa
(74) *Attorney, Agent, or Firm*—Mayer, Brown, Rowe & Maw LLP

(57) ABSTRACT

Process for the preparation of urea from ammonia and carbon dioxide, wherein the waste gases released at virtually atmospheric pressure in a urea plant are compressed by an ejector driven by the waste gas from the high-pressure synthesis and are supplied to a medium-pressure absorber. The pressure of the waste gases is increased by 0.15–1 MPa.

6 Claims, No Drawings

PROCESS FOR THE PREPARATION OF UREA

The invention relates to a process for the preparation of urea from ammonia and carbon dioxide.

Urea may be prepared by introducing excess ammonia along with carbon dioxide into a synthesis zone at a suitable pressure (for example 12–40 MPa) and a suitable temperature (for example 160–250° C.), which first results in the formation of ammonium carbamate according to the reaction:

$$2NH_3 + CO_2 \rightarrow H_2N-CO-ONH_4$$

Dehydration of the ammonium carbamate formed then results in the formation of urea according to the equilibrium reaction:

$$H_2N-CO-ONH_4 \leftrightarrow H_2N-CO-NH_2 + H_2O$$

The theoretically attainable conversion of ammonia and carbon dioxide into urea is determined by the thermodynamic position of the equilibrium and depends on for example the $NH_3/CO_2$ ratio (N/C ratio), the $H_2O/CO_2$ ratio and temperature.

In the conversion of ammonia and carbon dioxide to urea in the synthesis zone, a reaction product is obtained from the synthesis reactor which product is a urea synthesis solution which consists essentially of urea, water, ammonium carbamate and unbound ammonia.

Besides the aforementioned urea synthesis solution, there may evolve in the synthesis zone a gas mixture of unconverted ammonia and carbon dioxide along with inert gases, which gas mixture is also known as synthesis gas. The inert gases present in it may originate from for example a system that adds air to the plant in order to improve the plant's corrosion resistance. For example, inert gaseous components may be supplied to the synthesis zone via the raw materials (NH3 and CO2). Ammonia and carbon dioxide are removed from the synthesis gas and are preferably returned to the synthesis zone.

The synthesis zone may comprise separate zones for the formation of ammonium carbamate and urea. These zones may, however, also be united in a single apparatus. The synthesis may be effected in a single reactor or in two reactors. If two reactors are employed, the first reactor, for example, may be operated with virtually fresh raw materials and the second with raw materials that are completely or partly recirculated from for example the urea recovery.

The conversion of ammonium carbamate into urea and water in the synthesis reactor can be effected by ensuring a sufficiently long residence time for the reaction mixture in the reactor. The residence time will in general be longer than 10 min, preferably longer than 20 min. The residence time will in general be shorter than 3 hours, preferably shorter than 1 hour.

In practice, various processes are used for the preparation of urea. Initially, urea was prepared in so-called conventional high-pressure urea plants, which at the end of the 1960s were succeeded by processes carried out in so-called urea stripping plants.

A conventional high-pressure urea plant is understood to be a urea plant in which the decomposition of the ammonium carbamate that is not converted into urea and the expulsion of the customary excess ammonia take place at a substantially lower pressure than the pressure in the synthesis reactor itself. In a conventional high-pressure urea plant the synthesis reactor is usually operated at a temperature of 180–250° C. and a pressure of 15–40 MPa. In a conventional high-pressure urea plant, following expansion, dissociation and condensation at a pressure of between 1.5 and 10 MPa, the raw materials that are not converted into urea are returned to the urea synthesis as an ammonium carbamate stream. In addition, in a conventional high-pressure urea plant, ammonia and carbon dioxide are fed directly to the synthesis reactor. The N/C ratio in the urea synthesis in a conventional high-pressure urea process is between 3 and 5.

Initially, such conventional urea plants were designed as so-called 'Once-Through' processes. Here, non-converted ammonia was neutralised with acid (for example nitric acid) and converted into ammonium salts (for example ammonium nitrate). It did not take long until these conventional Once-Through urea processes were replaced with Conventional Recycle Processes, in which non-converted ammonia and carbon dioxide are recycled to the synthesis reactor as ammonium carbamate streams. In the recovery section, non-converted ammonia and carbon dioxide are removed from the urea synthesis solution obtained in the synthesis reactor, in which process a urea in water solution evolves. Next, this urea in water solution is converted into urea in the evaporation section by evaporating water at reduced pressure. Sometimes, the urea-water mixture is separated by means of crystallization techniques.

A urea stripping plant is understood to be a urea plant in which the decomposition of the ammonium carbamate that is not converted into urea and the expulsion of the customary excess ammonia largely take place at a pressure that is essentially virtually equal to the pressure in the synthesis reactor. This decomposition/expulsion takes place in a stripping zone with or without addition of a stripping gas. In a stripping process, carbon dioxide and/or ammonia may be used as stripping gas before these components are added to the synthesis reactor. Such stripping is effected in a stripper installed downstream of the synthesis reactor; in it, the urea synthesis solution coming from the synthesis reactor is stripped with the stripping gas with addition of heat. It is also possible to use thermal stripping here. Thermal stripping means that ammonium carbamate is decomposed and the ammonia and carbon dioxide present are removed from the urea solution exclusively by means of the supply of heat. Stripping may also be effected in two or more steps. In a known process a first, purely thermal stripping step is followed by a CO2 stripping step with further addition of heat. The ammonia and carbon dioxide-containing gas stream exiting from the stripper is returned to the reactor whether or not via a high-pressure carbamate condenser. Stripping of the urea synthesis solution with a stripping agent may take place in more than one stripper.

In a urea stripping plant the synthesis reactor is operated at a temperature of 160–240° C., preferably at a temperature of 170–220° C. The pressure in the synthesis reactor is 12–21 MPa, preferably 12.5–19.5 MPa. The N/C ratio in the synthesis zone in a urea stripping plant is between 2.5 and 4.

A frequently used embodiment for the preparation of urea by a stripping process is the Stamicarbon $CO_2$ stripping process as described in European Chemical News, Urea Supplement, of Jan. 17, 1969, pages 17–20. The greater part of the gas mixture obtained in the stripping operation is condensed and adsorbed, together with the ammonia required by the process, in a high-pressure carbamate condenser, after which the ammonium carbamate stream that has formed here is returned to the synthesis zone for the formation of urea.

The high-pressure carbamate condenser may de designed as, for example, a so-called submerged condenser as described in NL-A-8400839. The submerged condenser can be placed in horizontal or vertical position. It is, however, particularly advantageous to carry out the condensation in a horizontal submerged condenser (a so-called pool condenser; see for example Nitrogen No 222, July–August 1996, pp. 29–31), because, in comparison with other designs of this condenser, the liquid usually has a longer residence time in the pool condenser. This results in the formation of extra urea, which raises the boiling point, so that the difference in temperature between the urea-containing ammonium carbamate solution and the cooling medium increases, resulting in better heat transfer.

After the stripping operation, the pressure of the stripped urea synthesis solution is reduced to a low level in the urea recovery and the solution is concentrated by evaporation, after which urea is released and a low-pressure ammonium carbamate stream is recirculated to the synthesis section. Depending on the process, this ammonium carbamate may be recovered in either a single or a plurality of process steps operating at different pressures.

In the urea process, waste gases are formed as by-products in various locations in the plant. These waste gases are essentially inert gases, contaminated with ammonia and carbon dioxide, whose inert constituent components are vented to the atmosphere. Prior to being removed from the plant, these waste gases should first be rid of ammonia in particular.

The waste gases are often cleaned by an absorption step in what is known as an absorber, in which especially ammonia is removed from the waste gases with the aid of a suitable ammonia solvent such as water or weakly ammoniacal process condensate, with or without heat being removed by for example heat exchangers. Waste gases are formed at various pressure levels. It is advantageous for ammonia to be absorbed from these waste gases at as high a pressure as possible.

In the Stamicarbon $CO_2$ stripping process, for example, the gas stream from the reactor, the synthesis gas, is scrubbed in a scrubber at high pressure (>10 MPa) using an ammonium carbamate solution originating from the low-pressure section of the plant. In the high-pressure scrubber an ammonium carbamate stream is formed, which stream normally is passed to the high-pressure condenser and a non-condensed stream of waste gases. Prior to being vented to the atmosphere, the waste gases from the high-pressure scrubber are purified of the remaining ammonia by an absorption step in an absorber operating at medium pressure. 'At medium pressure' means at a pressure of for example 0.3–0.6 MPa.

Other examples in which waste gases are purified by an absorption step include the 'Self-stripping process' as described in Uhlmann's Encyclopedia of Industrial Chemistry, Vol A 27, pages 346–348, 1996, in which the waste gases from the high-pressure section of the plant are eventually also scrubbed in an absorber operating at medium pressure. Likewise, in the ACES process, as described Uhlmann's Encyclopedia of Industrial Chemistry, Vol A 27, pages 348–349, 1996, the waste gases, containing non-condensable components, vented from the high-pressure scrubber to the medium-pressure decomposition stage are eventually scrubbed in an absorber operating at medium pressure.

According to the current state of the art, the waste gases from the high-pressure section of the plant are passed to the medium-pressure absorber via control valves. A serious drawback is that the energy that potentially may be recovered is lost in the process.

Furthermore, ammonia-bearing gas streams are released in all urea plants at much lower pressures of between for example 0.1 MPa and 0.3 MPa, but mostly at atmospheric pressure. An example is the waste gas in the condensation zone of the evaporation section. In the evaporation section, the urea solution is concentrated by evaporation at reduced pressure, in which process there is formed a water vapour stream contaminated with ammonia from which the condensable components are condensed in a condenser. The remaining waste gas still contains ammonia, however. Other examples are the waste gas of the atmospheric storage tanks for aqueous ammonia or for urea solutions, the waste gas of screening equipment and centrifuges in the crystallization sections of urea plants and the like. A drawback of these streams is their low pressure (for example atmospheric), since a low pressure is disadvantageous in absorption processes.

It is increasingly required, for both economic and environmental reasons, to clear these low-pressure ammonia-bearing streams of ammonia before they are vented to the atmosphere. Here, too, absorption in a suitable solvent, such as water or weakly ammoniacal water, is a suitable cleaning technique. Such absorption is commonly carried out in an absorber operating at low pressure and may be further optimized by direct or indirect cooling by means of heat exchangers. 'At low pressure' means at a pressure of between 0.1 MPa and 0.3 MPa but mostly at virtually atmospheric pressure.

It has been found that the aforementioned drawbacks may be eliminated by increasing the pressure of the waste gases released in a urea plant at virtually atmospheric pressure with an ejector driven by the waste gas from the high-pressure synthesis section and supplying the said waste gases to a medium-pressure absorber. The pressure of the waste gases released at virtually atmospheric pressure is increased by between 0.15 MPa and 2 MPa, preferably between 0.2 and 0.5 MPa.

The expansion energy of the high-pressure waste gases is utilized here in an ejector by drawing in and compressing the low-pressure waste gases. As a consequence, the low-pressure waste gases arrive at a higher pressure level so that absorption of ammonia in the solvent is improved. The total ammonia losses from the urea plant are limited in this way.

In addition, the present process presents the advantage that the waste gases supplied to the two absorption steps are combined, so that the absorption is combined in a single item of equipment, resulting in lower investment for the urea plant.

Furthermore, the present process is highly suitable for improving and optimizing existing urea plants by increasing the pressure of the waste gases from an absorber operating at virtually atmospheric pressure with an ejector driven by the waste gas from the synthesis section and supplying the said waste gases to a medium-pressure absorber. The pressure of the waste gases from an absorber operating at virtually atmospheric pressure is increased here by between 0.15 MPa and 2 MPa, preferably between 0.2 and 0.5 MPa.

The invention may be applied in all existing urea processes, both conventional urea processes and urea stripping processes, because waste gas streams of various pressure levels and unnecessary energy losses and poor absorption results occur in all these processes.

Examples of conventional urea processes in which the invention may be applied are so-called 'Once-Through', Conventional 'Recycling' and Heat Recycling Processes.

Examples of urea stripping processes in which the invention may be applied are the $CO_2$ Strip process, the Ammonia Strip process, the Selfstripping process, the ACES (Advanced process for Cost and Energy Saving) process, the IDR (Isobaric-Double-Recycle) process and the HEC process.

The invention is illustrated by the following example.

EXAMPLE

In a urea plant with a capacity of 1500 MT per day, the waste gases obtained at atmospheric pressure were compressed with an ejector driven by the synthesis gas whereupon the compressed gases were absorbed in the existing 0.4 MPa absorber. As a result, the atmospheric absorber became redundant. Originally, there were two emission points in this plant: one at the 0.4 MPa absorber and the other at the atmospheric absorber. On account of the present process, one emission point was eliminated.

The process was carried out under the following conditions:

Synthesis gas as propellant for the ejector:
Flow rate: 1429 kilograms per hour
Pressure: 14 MPa
Temperature: 112° C.
Gas to be compressed (previously supplied to the atmospheric absorber):
Flow rate: 807 kilograms per hour
Pressure: atmospheric
Temperature: 114° C.
Gas compressed by ejector at inlet of 0.4 MPa absorber:
Flow rate: 2636 kilograms per hour
Pressure: 0.4 MPa
Temperature: 106° C.

It was found that application of the present process resulted in ammonia losses from this particular emission point of 2.45 kg/hour.

The ammonia losses for a 1500 MT per day plant with two emission points amounted to 4.2 kg/hour.

What is claimed is:

1. Process for the preparation of urea from ammonia and carbon dioxide, characterized in that in a plant for the preparation of urea the waste gases released at virtually atmospheric pressure are compressed by an ejector driven by the waste gas from the high-pressure synthesis and are supplied to a medium-pressure absorber.

2. Process according to claim 1, characterized in that the pressure of the waste gases released at virtually atmospheric pressure is increased by between 0.15 and 2 MPa.

3. Process according to claim 2, characterized in that the pressure of the waste gases released at virtually atmospheric pressure is increased by between 0.2 and 0.5 MPa.

4. Process for improving and optimizing existing urea plants by increasing the pressure of the waste gases from an absorber operating at virtually atmospheric pressure with an ejector driven by the waste gas from the synthesis and supplying the said waste gases to a medium-pressure absorber.

5. Process according to claim 4, characterized in that the pressure of the waste gases from an absorber operating at virtually atmospheric pressure is increased by between 0.15 MPa and 2 MPa.

6. Process according to claim 4, characterized in that the pressure of the waste gases from an absorber operating at virtually atmospheric pressure is increased by between 0.2 MPa and 0.5 MPa.

* * * * *